United States Patent [19]
Anderson

[11] 4,060,638
[45] Nov. 29, 1977

[54] ANTHRANILIC ACID AMIDES

[75] Inventor: Paul L. Anderson, Dover, N.J.

[73] Assignee: Sandoz, Inc., E. Hanover, N.J.

[21] Appl. No.: 580,873

[22] Filed: May 27, 1975

[51] Int. Cl.$^2$ .................. C07C 103/76; A61K 31/165
[52] U.S. Cl. ............................. 424/324; 260/558 A; 560/250; 424/311
[58] Field of Search .................. 260/558 A; 424/324

[56] References Cited

U.S. PATENT DOCUMENTS

| 3,192,214 | 6/1965 | Krapcho | 260/558 A X |
| 3,213,137 | 10/1965 | Neill | 260/558 A |
| 3,252,986 | 5/1966 | Gadeker | 260/558 A X |
| 3,828,042 | 8/1974 | Schlandecker et al. | 260/558 A X |

FOREIGN PATENT DOCUMENTS 1,091,120  10/1960  Germany .................. 260/558 A

OTHER PUBLICATIONS

*Medicinal Chemistry*, 3rd ed., Part I, pp. 71–72 (1969).
Yale; J., Med. and Pharm. Chem., vol. 1, No. 2, p. 121 (1959).

*Primary Examiner*—Allen B. Curtis
*Assistant Examiner*—Thomas A. Waltz
*Attorney, Agent, or Firm*—Gerald D. Sharkin; Richard E. Vila; Frederick H. Weinfeldt

[57] ABSTRACT

Derivatives of trifluoromethyl-substituted anthranilic acid amides, e.g., N-methyl-o-amino-$\alpha,\alpha,\alpha$-trifluoromethyl-p-toluamide, are useful as minor tranquilizers and muscle relaxants.

17 Claims, No Drawings

ANTHRANILIC ACID AMIDES

This invention relates to organic compounds and, more particularly to trifluoromethyl-substituted anthranilic acid amides, and to non-toxic pharmaceutically-acceptable acid addition salts thereof, where such may exist, as well as to intermediates in the preparation of such amides and to pharmaceutical preparations containing such amides.

The compounds of this invention may conveniently be represented by the formula I:

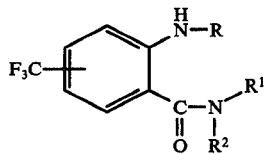

in which
R is a hydrogen atom, or lower alkanoyl;
$R^1$ is a hydrogen atom or alkyl; and
$R^2$ is alkyl or alkyl substituted by a hydroxy or alkanoyloxy function at a carbon atom other than the carbon atom adjacent to the nitrogen atom; provided that when R is alkanoyl then $R^2$ is alkyl or alkanoyloxyalkyl; the alkanoyl portion of $R^2$ being the same as R when it is alkanoyl, In the above-presented definitions of the substituents R, $R^1$ and $R^2$, it is to be understood that the term lower alkanoyl in the definition of R, or of the alkanoyl portion of $R^2$ when it is alkanoyloxy is intended to include alkanoyls having from 2 to 4 carbon atoms, e.g., acetyl, propionyl and butyryl, including isomeric forms where such exist, but are preferably unbranched; and the term alkyl in the definitions of $R^1$ and $R^2$ and the alkyl portion of $R^2$ when it is hydroxy-alkyl or alkanoyloxy-alkyl in the definitions of $R^2$ is intended to include alkyls having from 1 to 6 carbons, such as methyl, ethyl, propyl, butyl, pentyl and hexyl, including isomeric forms where such can exist; with particular respect to $R^2$ when it is hydroxyalkyl or alkanoyloxyalkyl, it is to be understood that the hydroxy or alkanoyloxy moiety can be attached to the alkyl portion at any carbon thereof, except the carbon bonded to the nitrogen atom, but it is preferred that it is attached to a secondary carbon atom, i.e., that the carbon atom of the alkyl portion bearing the oxygen atoms also bears one hydrogen atom, such as a 2-hydroxy n-butyl group.

The class of compounds I consist of two subclasses of compounds, depending on the nature of R, i.e., aminoamides of the formula Ia:

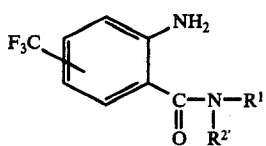

in which $R^1$ is as defined above; and $Rhu\ 2'$ is alkyl or hydroxyalkyl; and diamides of the formula Ib:

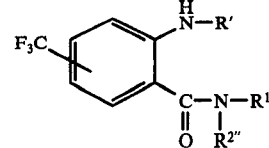

in $R^1$ is as defined above, $R'$ is alkanoyl and $R^{2''}$ is alkyl or alkanoyloxy.

It will be noted that compounds Ia bear a free amino group, and can, therefore, form non-toxic pharmaceutically-accepted salts of strong acids; it being understood that such salts are comprehended as being included within the scope of the invention.

Compounds Ia may be obtained by amidation (process a) of a corresponding ester of formula II:

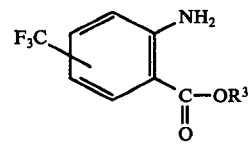

in which $R^3$ is a lower substituted alkyl group having from 1 to 4 carbon atoms, e.g., ethyl.

Process (a) involves reaction of a compound II with an amine of the formula III:

in which $R^1$ and $R^{2'}$ are as defined at a temperature, e.g., of from about 50° to 200° C. Where the amine (Compound III) is a liquid, it may serve as medium for the reaction. However, where the amine is not satisfactory for such purpose, an inert organic solvent, e.g., an aromatic hydrocarbon, such as benzene, toluene or xylene, or a cyclic ether, e.g., p-dioxane; or where the amine is water-miscible, water, may be used as the reaction medium. It is particularly convenient to carry out the reaction at the reflux temperature of the reaction mixture, when such falls within the suitable temperature range.

Compounds Ib may be obtained by alkanoylation process b) of a compound Ia with an alkanoylating agent, i.e., a compound IV

  R'—X  IV in which R' is as defined above, i.e., it is the same as R when it is not a hydrogen atom, and X is chloro, bromo or

  —O—R' in which R' is as defined above.

The alkanoylation of compounds Ia (process b); may be carried out by conventional techniques. Th alkanoylation, thus, may be effected by processes per se for the alkanoylation of aliphatic alcohols or amines. Suitable alkanoylating agents (IV) include organic acids, acyl halides and acid anhydrides and mixtures thereof. For example, where the desired alkanoyl moiety is acetyl, a preferred alkanoylating agent is acetic anhydride. In carrying out the alkanoylation, inert solvent may be employed or excess alkanoylating agent may serve as solvent. An acid binding agent, e.g., pyridine, is preferably used. Preferred temperatures vary between −10° and 50° C. If desired, more stringent conditions may be used, characterized by the presence of a strongly acidic catalyst, e.g., p-toluene-sulphonic acid, in which case the acid-binding agent is omitted.

It will be noted that when the $R^2$ substituent of a compound Ia is hydroxyalkyl, then alkanoylation will occur concurrently at both the amino function and the hydroxy function. Hence, when $R^{2''}$ is alkanoyloxyalkyl, the alkanoyl portion thereof will be the same as $R'$. Alkanoylating agents are used in amounts of at least the chemical equivalents required for the alkanoylation, and preferably in substantial excess.

Conversely, where desired, the alkanoylated forms of Compounds I, may be hydrolyzed (process c) employing conventional means, e.g., by treatment with dilute sodium or potassium hydroxide or methanolic potassium bicarbonate, to obtain corresponding amino or hydroxy-bearing forms of Compounds I. Process (c) is conveniently carried out in the presence of a water-miscible co-solvent, e.g., a lower alkanol, such as ethanol, at temperatures of from about 100° to 160° C.

The above-described ester starting materials, Compounds II, are obtainable by esterifying (process d) a corresponding trifluoromethyl anthranilic acid of the formula V:

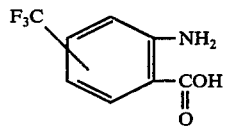

by reaction with an alcohol, i.e., a compound VI of the formula:

HO—R³             VI in which $R^3$ is as defined above, under conditions conventionally employed in esterifying a carboxylic acid function. Process (d) may conveniently be carried out in an inert organic solvent, for example, an aromatic hydrocarbon such as toluene, benzene or xylene, in the presence of an acidic catalyst such as an aromatic sulfonic acid, e.g., p-toluene sulfonic acid, at elevated temperatures, e.g., from 100° to 200° C, under conditions in which water formed in the reaction is removed from the system, e.g., by carrying out process (d) in an extractor apparatus charged with a drying agent. It is particularly convenient to carry out the esterification at the reflux temperature of the reaction mixture, when such falls within a suitable range. Reaction times will, of course, vary with the nature of the reactants and the reaction conditions employed, but it is preferred to carry out the reaction at more moderate temperatures, e.g., at from about 120° to 150° C over an extended period of time, e.g., for from about 1 to 20 days.

The products of the above-described reactions may be recovered and refined in conventional manner, e.g., by crystallization, distillation or chromatographic techniques, such as eluting from a chromotographic column or separating on a silica layer.

Starting materials and reagents used in the above-described reactions, e.g., Compounds III, IV, V and VI are either known and obtained by methods described in the literature, or where not known, may be obtained by methods analogous to those described in the literature.

Some of the reactants and starting materials are commercially available.

It will be noted that the trifluoromethyl substituent can be located at any one of the 3-, 4-, 5-, and 6- positions of the anthranilic acid nucleus, preferably at the 4-position. The above-described series of reactions (process a through d) are conveniently represented in the following Reaction Scheme wherein $R'$, $R^1$, $R^2$, $R^{2'}$, $R^{2''}$ and $R^3$ are defined above:

REACTION SCHEME

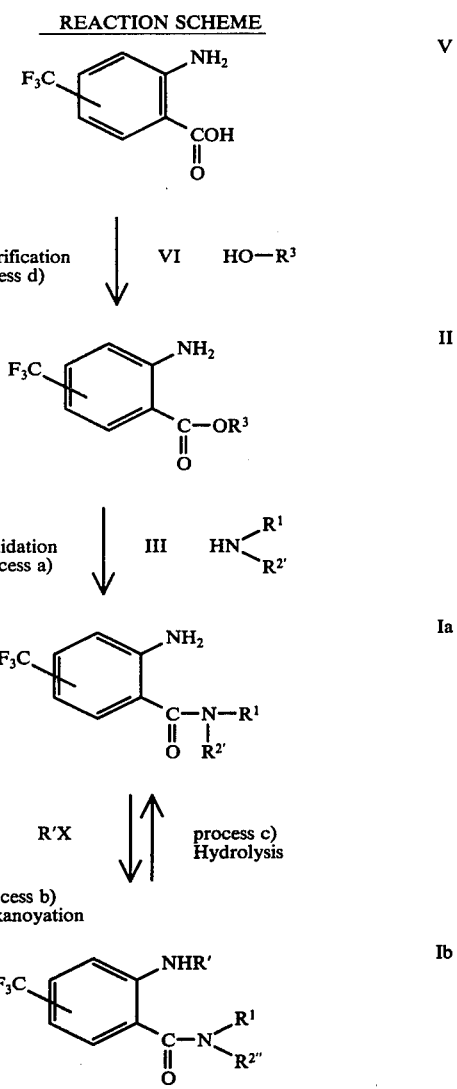

STATEMENT OF UTILITY

The compounds of formula (I) are useful because they possess pharmacological activity in animals. In particular, the compounds are useful as minor tranquilizers and muscle relaxants as indicated (1) by docility, ataxia, loss of righting reflex and hind leg placing results in behavior tests in mice given from about 10 to b 200 mg per kilogram of animal body weight, i.p. of the test compound according to the 30-word adjective check sheet system basically a described by Irwin, S. (Gordon Research Conference, Medicinal Chemistry (1959) and Chen (Symposium on Sedative and Hypnotic Drugs, Williams and Wilkins, 1954); (2) by a reduction of hexobarbital anesthesia in mice (10 to 200 mg./kg.) according to the method of Winter (J. Pharmacol & Exp.

Therap., 97:7, 1948); (3) by an inhibition of chemically induced seizures in mice on intraperitoneal administration (10–200 mg./kg.) using 50 mg./kg. of N-sulfamoylazepine to induce seizures; and (4) by a neurological deficit and muscle relaxation in the "rotarod test" in mice on administration intraperitoneally (10–150 mg./kg.) essentially according to the method of Dunham et al., J. Am. Pharm. Assoc. 45:208, 1957.

For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained when administered at a daily dosage of from about 2 milligrams to about 200 milligrams per kilogram of animal body weight, preferably given orally and in divided doses, 2 to 4 times a day, or in sustained release form. For large mammals, the total daily dose is from about 140 milligrams to about 1,500 milligrams of the compound, and the dosage forms suitable for internal administration comprise from about 35 to 750 mg of the compound in admixture with the solid or sterile liquid, pharmaceutically acceptable carrier or diluent.

For the above uses, compounds I may be administered orally in such forms as tablets, dispersible powders, granules, capsules, syrups and elixirs; and parenterally as solutions, suspensions, dispersions, emulsions, and the like, e.g., a sterile injectable formulation such as an aqueous suspension. These pharmaceutical compositions may contain from about 0.5% up to about 90% of the active ingredient in combination with the carrier or adjuvant, more usually between 10% and 60% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation.

Convenient unit dosage forms for the above-described uses are those having from about 35 to 750 mg, e.g., about 50 to 500 mg of a compound I as active ingredient. The preferred pharmaceutical compositions from the standpoint of preparation and ease of administration are solid orally administrable compositions, particularly tablets and solid or liquid diluent-filled capsules (as appropriate to the nature of the particular active ingredient), containing, e.g., from about 35 to 750 mg of the active ingredient.

Pharmaceutically acceptable acid addition salts of the compounds I where such can exist (i.e., those salts which do not significantly increase the toxicity of the basic compound) are included with the scope of this invention. Included are salts of strong acids, e.g., with inorganic acids, e.g., the hydrochloride, hydrobromide, phosphate and sulfate salts and salts with organic sulfonic acids, methanesulfonate, ethanesulfonate, benzenesulfonate and p-toluenesulfonate salts. It is to be understood that such salts are included within this invention as they have the same activity, and may be used in the same manner as their free base forms. Such salts may be prepared by conventional means, such as by reaction with a suitable acid.

Tablets and capsules containing the ingredients indicated below may be prepared by conventional techniques and are useful as muscle relaxants and in treating tension and anxiety at a dose of one tablet or capsule 2 to 4 times a day.

| Ingredient | Weight in Milligrams Tablet | Capsule |
|---|---|---|
| N-methyl-o-amino-$\alpha,\alpha,\alpha$-trifluoro-p-toluamide | 100 | 100 |
| Tragacanth | 10 | — |
| Lactose | 147.5 | 120 |
| Corn Starch | 25 | — |
| Talcum | 15 | — |
| Magnesium Stearate | 2.5 | — |

In the following examples, which are illustrative of the invention, temperatures are in degrees centigrade, and room temperature is 20° to 30° C, unless indicated otherwise.

EXAMPLE 1

N-(2-hydroxybutyl)-o-amino-$\alpha,\alpha,\alpha$-trifluoro-p-toluamide

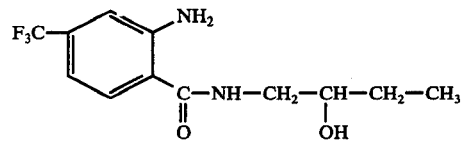

(Step A) 4-trifluoromethyl anthranilic acid ethyl ester 19.8 grams of 4-trifluoromethylanthranilic acid are dissolved in 350 ml of anhydrous ethanol and 300 ml of dry toluene. To this solution is added 21.8 grams of anhydrous p-toluenesulfonic acid. The solution is refluxed under an extractor containing a thimble of anhydrous magnesium sulfate for 2 weeks with periodic replacement of the drying agent. The solvent is then removed on a rotary evaporator. The residue is treated with 200 ml of 2N sodium hydroxide. The resultant mixture is extracted thrice with combined 75 ml portions of diethylether. The combined extracts are washed with 2N sodium hydroxide, then distilled water and finally brine. The organic solution is dried over anhydrous potassium carbonate. The drying agent is filtered off, and the solvent is removed on a rotary evaporator. The resultant oil is chromatographed on a filter column of silica gel with chloroform as the eluant. The first fractions contain 4-trifluoromethylanthranilic acid ethyl ester, which is recovered by crystallization. Melting Point: 42°–43° C.

(Step B)
N-(2-hydroxybutyl)-o-amino-$\alpha,\alpha,\alpha$-trifluoro-p-toluamide One gram of 4-trifluoromethylanthranilic acid, ethyl ester is dissolved in 20 ml of 1-amino-2-butanol. The solution is refluxed under a nitrogen atmosphere for 22 hours. The excess amino-butanol is distilled off under reduced pressure to yield a brown oil. Water is added to the residue resulting in solidification of the material. The solids are filtered off, washed with water, and air dried with suction. The solids which are so obtained are dissolved in methylene chloride, the solution is decolorized with charcoal, and the title product crystallized from the filtered and concentrated solution, melting point 132°–134°.

EXAMPLE 2

N-methyl-o-amino-α,α,α-trifluoro-p-toluamide

One gram of 4-trifluoromethyl anthranilic acid, ethyl ester is dissolved in 50 ml of 40% aqueous methylamine. The solution is refluxed overnight. The solvent is removed from the reaction mixture under reduced pressure. The resulting residue is chromatographed on preparative thin layer plates (silica gel G) using 2% methanol/chloroform as the solvent system to yield the title product (which may also be called, 4-trifluoromethyl-2-amino-benzoic acid, methylamide). Melting Point: 114°–115°.

Repeating the procedure of this example, but using in place of the 4-trifluoromethyl anthranilic acid ethyl ester, an approximately equal amount of a. 3-trifluoromethyl anthranilic acid ethyl ester;
b. 5-trifluoromethyl anthranilic acid ethyl ester; or
c. 6-trifluoromethyl anthranilic acid ethyl ester; there is accordingly obtained:

a. N-methyl-2-amino-α,α,α-trifluoro-3-toluamide;
b. N-methyl-2-amino-α,α,α-trifluoro-5-toluamide; and
c. N-methyl-2-amino-α,α,α-trifluoro-6-toluamide.

EXAMPLE 3

N-(2-acetoxybutyl)-2-acetylamino-α,α,α-trifluoro-p-toluamide

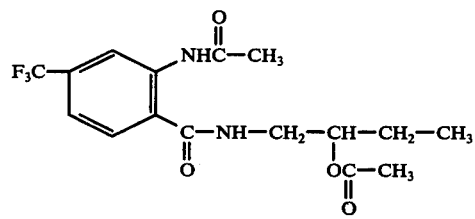

To 1.0 g. of N-(2-hydroxybutyl)-o-amino -α,α,α-trifluoro-p-toluamide dissolved in 75 ml. of pyridine, is added 15 ml. of acetic anhydiride and the solution is stirred 17 hours at room temperature. Residual acetic anhydride and pyridine are then removed by distillation and the resulting solids dried under high vacuum to obtain the title product, m.p. 121°.

Carrying out the above-described procedure using N-methyl-o-amino-α,α,α-trifluoro-p-toluamide (obtainable by Example 2), there is accordingly obtained N-methyl-o-acetoamino-α,α,α-trifluoro-p-toluamide.

What is claimed is:

1. A compound which is a free base of the formula

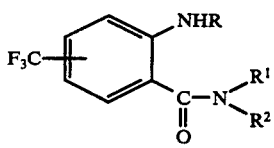

in which

R is a hydrogen atom, or alkanoyl having from 2 to 4 carbon atoms;
R$^1$ is a hydrogen atom or alkyl having from 1 to 6 carbon atoms; and
R$^2$ is alkyl having from 1 to 6 carbon atoms or hydroxy-alkyl having from 1 to 6 carbon atoms, the hydroxy function being located at a carbon atom other than the carbon atom adjacent to the nitrogen atom; provided that when R is alkanoyl then R$^2$ is alkyl;

or a non toxic pharmaceutically acceptable acid addition salt thereof when R is a hydrogen atom.

2. A compound of claim 1 in which R is a hydrogen atom.
3. A compound of claim 1 in which R is alkanoyl.
4. A compound of claim 1 in which the trifluoromethyl group is at the 4-position.
5. A compound of claim 1 in which R$^2$ is alkyl.
6. A compound of claim 1 in which R$^2$ is hydroxyalkyl.
7. The compound of claim 6 which is N-(2-hydroxybutyl)-o-amino-α,α,α-trifluoro-p-toluamide.
8. The compound of claim 1 which is N-methyl-o-amino-α,α,α-trifluoro-p-toluamide.
9. A pharmaceutical composition which is useful as a minor tranquilizer in a mammal comprising from about 35 to 750 milligrams of a compound which is a free base of the formula in which R is a hydrogen atom, or alkanoyl having from 2 to 4 carbon atoms;
R$^1$ is a hydrogen atom or alkyl having from 1 to 6 carbon atoms; and
R$^2$ is alkyl having from 1 to 6 carbon atoms or hydroxy-alkyl having from 1 to 6 carbon atoms, the hydroxy function being located at a carbon atom other than the carbon atom adjacent to the nitrogen atom; provided that when R is alkanoyl then R$^2$ is alkyl;

or a non-toxic pharmaceutically acceptable acid addition salt thereof when R is a hydrogen atom, and a pharmaceutically acceptable carrier.

10. A composition of claim 9 which is a unit dosage form in which the compound is present in an amount of from about 50 to 500 milligrams.
11. A composition of claim 9 which is solid and orally administrable.
12. A composition of claim 11 in the form of a tablet or capsule.
13. A composition of claim 12 in which the compound is N-methyl-o-amino-α,α,α-trifluoro-p-toluamide.
14. A method of treating anxiety in a mammal in need of such treatment which comprises internally administering an amount of a compound which is a free base of the formula

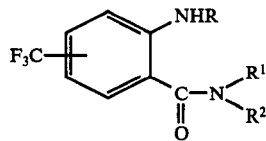

in which
R is a hydrogen atom, or alkanoyl having from 2 to 4 carbon atoms;
R¹ is a hydrogen atom or alkyl having from 1 to 6 carbon atoms; and
R² is alkyl having from 1 to 6 carbon atoms or hydroxy-alkyl having from 1 to 6 carbon atoms, the hydroxy function being located at a carbon atom other than the carbon atom adjacent to the nitrogen atom; provided that when R is alkanoyl then R² is alkyl;

or a non-toxic pharmaceutically acceptable acid addition salt thereof when R is a hydrogen atom, effective in relieving anxiety in said mammal.

15. A method of claim 14 in which the compound is administered in an amount of from about 140 to 1,500 milligrams per day.

16. A method of claim 14 in which the compound is administered orally.

17. A method of claim 14 in which the compound is N-methyl-o-amino-α,α,α-trifluoro-p-toluamide.

* * * * *